United States Patent [19]

Schleppinghoff et al.

[11] Patent Number: 5,012,031
[45] Date of Patent: Apr. 30, 1991

[54] PROCESS FOR THE PREPARATION OF TERT.-OLEFINS

[75] Inventors: Bernhard Schleppinghoff; Hans-Ludwig Niederberger; Christian Gabel, all of Dormagen; Peter M. Lange, Leverkusen; Alfred Mitschker, Odenthal-Holz, all of Fed. Rep. of Germany

[73] Assignees: EC Erdoelchemie GmbH, Cologne; Bayer Aktiengesellschaft, Leverkusen, both of Fed. Rep. of Germany

[21] Appl. No.: 320,262

[22] Filed: Mar. 7, 1989

[30] Foreign Application Priority Data

Mar. 15, 1988 [DE] Fed. Rep. of Germany ....... 3808498

[51] Int. Cl.$^5$ ................................................ C07C 1/24
[52] U.S. Cl. .................................................... 585/639
[58] Field of Search ......................................... 585/639

[56] References Cited

U.S. PATENT DOCUMENTS

| | | | |
|---|---|---|---|
| 4,447,668 | 5/1984 | Smith, Jr. et al. | 585/639 |
| 4,570,026 | 2/1986 | Keyworth et al. | 585/639 |
| 4,629,710 | 12/1986 | Smith, Jr. | 585/639 |
| 4,751,343 | 6/1988 | Reinhardt et al. | 585/639 |

FOREIGN PATENT DOCUMENTS 0102840 3/1984 European Pat. Off. ............ 585/639

*Primary Examiner*—Asok Pal
*Attorney, Agent, or Firm*—Sprung Horn Kramer & Woods

[57] ABSTRACT

Tert.-olefins are obtained in high purity by cleavage of their alkyl ethers, when the catalysts used for this purpose are styrene/divinylbenzene resins which contain sulphonic acid groups and have a macroporous structure and the polymer matrix of which has an internal surface area of at least 400 m$^2$/g, a pore volume (porosity) of 0.6-2.5 ml/g and a mean pore diameter of 40-1000 Å. These catalysts show long service lives.

19 Claims, No Drawings

PROCESS FOR THE PREPARATION OF TERT.-OLEFINS

BACKGROUND OF THE INVENTION

The present invention relates to a process for the preparation of tert.-olefins by cleavage of their alkyl ethers over specific catalysts which very sharply suppress the formation of the undesired dialkyl ethers and at the same time have a long service life.

It has been known for a long time to obtain tert.-olefins from distillate cuts (for example from product streams of crackers) in a pure form in such a way that they are first selectively converted with alkanols into their alkyl ethers and these alkyl ethers are then cleaved again after they have been separated from the remaining distillate cut. Acidic cation exchangers, for example styrene/divinylbenzene resins containing sulphonic acid groups, have been disclosed as cleavage catalysts, apart from other catalysts.

All cleavage catalysts form, from the alkanol liberated in the cleavage, the respective dialkyl ether which is more volatile than the underlying alkanol and hence accompanies and contaminates the tert.-olefin which is separated off as the top product by distillation. To a particularly great extent, this applies to dimethyl ether, which arises in the cleavage of methyl tert.-butyl ether (MTBE) or tert.-amyl methyl ether (TAME) and which contaminates the desired i-butene or tert.-amylene respectively.

In attempts to suppress the formation of these dialkyl ethers, only catalysts were obtained which lost their activity and selectivity with respect to the production of pure tert.-olefines to such an extent after a few days, frequently only a few hours, that they are completely unsuitable for low-cost continuous processes. It therefore appeared as though it was impossible to resolve the "dilemma", namely having to accept the disadvantage of the extensive contamination of the tert.-olefin by the dialkyl ether or having to accept the disadvantage of the intolerably short service lives of the catalyst.

SUMMARY OF THE INVENTION

It has now been found, surprisingly, that both disadvantages can be eliminated simultaneously if the cleavage catalysts used are those described below.

Thus, a process for the preparation of tert.-olefins of the formula

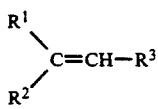   (I)

by cleavage of their alkyl ethers of the formula

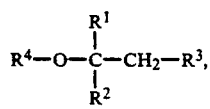   (II)

wherein, in the two formulae, $R^1$, $R^2$, $R^3$ and $R^4$ independently of one another denote straight-chain or branched $C_1$-$C_4$-alkyl and $R^3$ can additionally denote hydrogen, at an elevated temperature over styrene/divinylbenzene resins, containing sulphonic acid groups, as catalysts has been found, which is characterized in that the catalysts used are those which have a macroporous structure and the polymer matrices of which have an internal surface area of at least 400 $m^2/g$, preferably 400–1000 $m^2/g$, a pore volume (porosity) of 0.6–2.5 ml/g, preferably 1–1.8 ml/g, and a mean pore diameter of 40–1000 Å, preferably 40–300 Å.

DETAILED DESCRIPTION OF THE INVENTION

Such polymer matrices can be prepared by known methods and provided with sulphonic acid groups by means of known sulphonating agents (gaseous $SO_3$, oleum, $H_2SO_4$, $ClSO_3H$ and others). In a preferred manner, the sulphonation is carried out with 80–100% strength, particularly preferably 85–95% strength, $H_2SO_4$ at 20°–180° C., preferably 80°–120° C. The said preparation conditions of the catalyst resins, which are to be employed according to the invention, represent a selection of processes carried out industrially and are thus feasible and inexpensive in a simple manner. The conditions of the sulphonation lead not only to a sulphonation in the surface region, but the polymer particle is not sulphonated in the core region in the same way as on the surface; significant sulphonation is thus achieved in an outer region which comprises about ⅓ to ½ of the particle radius. The sulphonation values are here adjusted to 1–2.5 milliequivalent/g, preferably 1.3–1.9 milliequivalent/g.

The process according to the invention is carried out at 60°–180° C. in the gas phase or in the liquid phase, with subsequent separation of tert.-olefin and alkanol (accompanied by a little unconverted ether which is recycled) by distillation. The reaction temperature is made dependent above all on the boiling points of the reactants. The upper region of 90°–180° C., preferably 100°–170° C., particularly preferably 100°–160° C., is applicable above all for the gas phase. For the liquid phase, above all the lower region is applicable which, however, can be extended up to 180° C. by working under pressure. For example, temperatures of 60°–180° C., preferably 60°–170° C., particularly preferably 70°–120° C., are mentioned for the liquid phase, it being possible to operate under a pressure of 1–20 bar, preferably 1–10 bar, particularly preferably 1–5 bar, depending on the boiling point. For this purpose, it is possible to operate at the autogenous pressure being established at the selected reaction temperature or additionally to apply an inert gas pressure ($N_2$, $H_2$).

Operation in the liquid phase under the autogenous system pressure being established is preferred. For this purpose, a liquid hourly space velocity (LHSV) of 1–50 liters of alkyl ether per hour and liter of catalyst, preferably 2–20 l/hour×liter, particularly preferably 2–15 l/hour×liter, is set in a continuous procedure.

The process according to the invention is carried out in conventional reaction apparatus. For the case of the catalyst being arranged in a fixed bed, inert material can be admixed to the catalyst particles or catalyst layers can be interrupted by inert layers. Examples of inert materials are $Al_2O_3$, steel bodies, ceramic bodies, and the like.

Possible alkyl ethers which are to be cleaved are preferably those in which $R^1$ and $R^3$ denote methyl, it being possible for $R^3$ additionally to denote hydrogen, and $R^2$ denotes $C_1$-$C_3$-alkyl, particularly preferably $C_1$-$C_2$-alkyl. Possible further alkyl ethers which are to be cleaved are preferably those in which $R^4$ denotes $C_1$–$C_3$-alkyl, particularly preferably $C_1$–$C_2$-alkyl.

The catalysts to be employed according to the invention have service lives of several months at high selectivity for the preparation of tert.-olefins, with very low formation of dialkyl ethers. As an example, the formation of dimethyl ether (DME) from MTBE or TAME may be mentioned which, in the case of conventional acidic cation exchangers, led to a content of 0.6–1% by weight of DME in the i-butene or i-amylene, respectively, taken off as the top stream, whereas the process according to the invention gives a content of less than 1000 ppm, frequently less than 500 ppm, of DME.

EXAMPLE 1

104 g of a porous bead polymer based on styrene/divinylbenzene and having a surface area of 600 m²/g, a pore volume of 1.6 ml/g and a mean pore diameter of 110 Å, were heated together with 500 ml of 93% strength $H_2SO_4$ to 100° C. and then stirred for 1 hour at this temperature. After cooling of the reaction mixture, excess $H_2SO_4$ was siphoned off, and the sulphonated resin was introduced into ice water. The remaining $H_2SO_4$ was then eluted in a column apparatus by means of deionized water. The resin was then dried at 80° C. in a drying cabinet. This gave a cation exchanger, the aromatic nuclei of which had been sulphonated to the extent of 27.8%; this corresponds to 1.8 milliequivalent/g.

EXAMPLE 2

The sulphonation according to Example 1 was repeated, but the reaction mixture was stirred for 6 hours at 120° C. In this case, the aromatic nuclei had been sulphonated to the extent of 40%.

EXAMPLE 3

The sulphonation according to Example 1 was repeated, but the reaction mixture was stirred for 6 hours at 180° C. In this case, the aromatic nuclei had been sulphonated to the extent of 42%; this corresponds to 2.56 milliequivalent/g.

EXAMPLE 4

TAME Cleavage in the Gas Phase over a Catalyst According to Example 1

A temperature-controllable flow reactor was used as the alkyl ether cleavage reactor. At a given internal reactor diameter of 18 mm, the catalyst bed height was selected such that the catalyst packing amounted to 150 ml. For a temperature monitoring, the reactor was fitted with several temperature measuring points. The reaction pressure established itself automatically, in accordance with the pressure drop across the catalyst bed. The substrate was metered in by means of a piston pump and heated to the reaction temperature in a preheater. The composition of the reaction product obtained at the reactor outlet was investigated by gas chromatography.

The tert.-amyl methyl ether (TAME) to be cleaved had the following composition:
TAME: 98% by weight
TAA (tert.-amyl alcohol): 0.9% by weight
tert. $C_7$-ether: 0.5% by weight
methanol: 0.1% by weight
water: 0.1% by weight
benzene: 0.2% by weight
other hydrocarbons: 0.2% by weight Independently of the catalyst loading states investigated (loading=ml of substrate/ml of catalyst × hour), less than 500 ppm of DME (dimethyl ether) were found in the reaction product. The DME content of the reaction product for various loadings of the catalyst is given in the table. For comparison, the DME content in the reaction product from TAME cleavage on a commercially available ion exchanger resin (SPC 118 from Bayer AG) was also included in the table. The reaction temperature was between 120° and 150° C.

| Catalyst | LHSV [ml/ml × h] | DME content ppm by mass |
| --- | --- | --- |
| Catalyst according to Example 1 | 14.7 | <100 |
|  | 8.7 | 140 |
|  | 5.0 | 320 |
| SPC 118 | 7 | 3000 |

The service life of the catalyst according to Example 1 is extremely long. No deactivation was to be found during a test running period of more than 600 hours.

(Comparison Example)

EXAMPLE 5

MTBE Cleavage and Simultaneous Methanol Extraction in a Column

In the cleavage column described below, MTBE was cleaved into i-butene and methanol over 90 days:

A steel pressure column provided with distillation and extraction devices and having an internal diameter of 50 mm was provided in the bottom circulation with a bed of cleavage catalyst. The bottom circulation also included the indirect bottom heating. Three column sections of 1 meter each were mounted on the evaporator. The column had 20 actual trays and was designed for an operating pressure of up to 20 bar. At the top of the column, water was fed which was taken off again in the middle; this water contained the predominant part of the methanol produced in the cleavage. The MTBE to be cleaved was fed to the column via the bottom. The i-butene formed in the cleavage was taken off at the column top. Reaction conditions:
MTBE feed (by gas chromatography): 99.9% by weight
wash water/MTBE ratio: 1:1
bottom temperature (cleavage temperature): 94° C.
top temperature: 39.5° C.
column pressure: 3.5 bar
reflux ratio: 6.0
catalyst quantity: 0.5 l
LHSV [ml/ml×h]: 8.0

The cleavage catalyst used was strongly acidic, macroporous, commercially available SPC 118 from Bayer.

The i-butene obtained as the top product was analysed by gas chromatography and had the following composition:
i-butene: 99.4% by weight
dimethyl ether: 0.58% by weight
$H_2O$: 0.02% by weight This composition was constant during the entire running period.

EXAMPLE 6

The experiment was carried out in the same way as that described in Example 5, and the cleavage catalyst used was that according to Example 1.

The composition of the top product obtained in this case was as follows:
i-butene: 99.9% by weight
dimethyl ether: 0.03% by weight
water: 0.02% by weight This composition remained constant for the entire investigation period of 90 days, and no decay of catalyst activity was detectable.

What is claimed is:

1. A process for the preparation of tert.-olefins of the formula

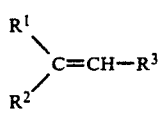

by cleavage of their alkyl ethers of the formula

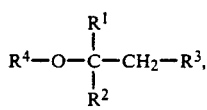

wherein, in the two formulae, $R^1$, $R^2$, $R^3$ and $R^4$ independently of one another denote straight-chain or branched $C_1$-$C_4$-alkyl and $R^3$ can additionally denote hydrogen, at an elevated temperature over styrene/divinylbenzene resins, containing sulphonic acid groups, as catalysts, characterized in that the catalysts used are those which have a macroporous structure and the polymer matrices of which have an internal surface area of at least 400 m²/g, a pore volume (porosity) of 0.6–2.5 ml/g and a mean pore diameter of 40–1000 Å, and have sulphonation values of 1–2.5 milliequivalent/g.

2. The process according to claim 1, characterized in that the mean pore diameter is 40–300 Å.

3. The process according to claim 1, characterized in that the pore volume (porosity) is 1–1.8 ml/g.

4. The process according to claim 1, characterized in that the internal surface area is 400–1000 m²/g.

5. The process according to claim 1, characterized in that the sulphonic acid groups are introduced by treating the matrix with 80–100% strength $H_2SO_4$ at 20°–180° C.

6. The process according to claim 5, characterized in that the sulphonic acid groups are introduced by treating the matrix with 85–95% strength $H_2SO_4$.

7. The process according to claim 5, characterized in that the sulphonic acid groups are introduced by treating the matrix at 80°–120° C.

8. The process according to claim 1, characterized in that the cleavage is carried out at 60°–180° C. in the liquid phase or gas phase.

9. The process according to claim 8, characterized in that the cleavage is carried out in the liquid phase at 60°–180° C., and under a pressure of 1–20 bar.

10. The process according to claim 9, characterized in that the cleavage is carried out at 60°–170° C.

11. The process according to claim 10, characterized in that the cleavage is carried out at 70°–120° C.

12. The process according to claim 9, characterized in that the liquid hourly space velocity (LHSV) is adjusted to 1–50 liters of alkyl ether per hour per liter of catalyst.

13. The process according to claim 12, characterized in that the LHSV is adjusted to 2–20 l/hour×liter of catalyst.

14. The process according to claim 13, characterized in that the LHSV is adjusted to 2–15 l/hour×liter of catalyst.

15. The process according to claim 1, characterized in that $R^1$ and $R^3$ denote methyl, it being possible for $R^3$ additionally to denote hydrogen, and $R^2$ denotes $C_1$-$C_3$-alkyl.

16. The process according to claim 15, characterized in that $R^2$ denotes $C_1$-$C_2$-alkyl.

17. The process according to claim 1, characterized in that $R^4$ denotes $C_1$-$C_3$-alkyl.

18. The process according to claim 17, characterized in that $R^4$ denotes $C_1$-$C_2$-alkyl.

19. The process according to claim 1, characterized in that the sulphonation values are adjusted to 1.3–1.9 milliequivalent/g.

* * * * *